United States Patent
Kim et al.

(10) Patent No.: US 10,330,611 B2
(45) Date of Patent: Jun. 25, 2019

(54) AUTOMATIC X-RAY INSPECTION APPARATUS FOR SMT INLINE PROCESS

(71) Applicant: SEC CO., LTD., Gyeonggi-do (KR)

(72) Inventors: Jong-hyun Kim, Gyeonggi-do (KR); Man-seok Kim, Gyeonggi-do (KR); Ki-ung Ryu, Gyeonggi-do (KR); Ki-jun Ryu, Gyeonggi-do (KR)

(73) Assignee: SEC CO., LTD., Gyeonggi-do (KR)

( * ) Notice: Subject to any disclaimer, the term of this patent is extended or adjusted under 35 U.S.C. 154(b) by 1003 days.

(21) Appl. No.: 14/366,614

(22) PCT Filed: Dec. 21, 2012

(86) PCT No.: PCT/KR2012/011255
§ 371 (c)(1),
(2) Date: Jun. 18, 2014

(87) PCT Pub. No.: WO2013/095035
PCT Pub. Date: Jun. 27, 2013

(65) Prior Publication Data
US 2015/0003578 A1    Jan. 1, 2015

(30) Foreign Application Priority Data
Dec. 22, 2011 (KR) .................. 10-2011-0139909

(51) Int. Cl.
*G01N 23/046* (2018.01)
(52) U.S. Cl.
CPC ..... *G01N 23/046* (2013.01); *G01N 2223/419* (2013.01)
(58) Field of Classification Search
CPC .. G01N 2223/419; G01N 23/046; H01J 37/18
See application file for complete search history.

(56) References Cited

U.S. PATENT DOCUMENTS 6,325,537 B1 * 12/2001 Watanabe ............ A61B 6/4233
                                                      378/196
6,459,759 B1 * 10/2002 Tominaga ............ G01N 23/046
                                                       378/22
(Continued)

FOREIGN PATENT DOCUMENTS

JP          05035302        2/1993
JP          10512532 A     12/1998
(Continued)

OTHER PUBLICATIONS

Chu et al., "Parallel Implementation for Cone Beam based 3D Computed Tomography (CT) Medical Image Reconstruction on Multi-core Processors", WC 2009, IFMBE Proceedings 25/IV, (2009), pp. 2066-2069.*

(Continued)

*Primary Examiner* — Chih-Cheng Kao
(74) *Attorney, Agent, or Firm* — Ohlandt, Greeley, Ruggiero & Perle, L.L.P.

(57) ABSTRACT

The invention relates to an automatic X-ray inspection apparatus for a SMT inline process, comprising: a stage unit for supporting an object to be inspected such that the object is attachable/detachable, the stage unit being movable on an X-axis and Y-axis in a plane and rotatable; an X-ray vacuum tube arranged beneath the stage unit so as to irradiate the object arranged on the stage unit with X-rays; and a detector arranged above the stage unit so as to swivel toward one side in order to detect X-rays transmitted through the object. The X-ray vacuum tube swivels in synchronization with the swiveling of the detector, and an X-ray emission surface of the X-ray vacuum tube is arranged so as to be parallel to the stage unit. The stage unit has a hollow shaft, and a hollow bearing that supports the hollow shaft such that the hollow shaft is rotatable.

9 Claims, 14 Drawing Sheets

(56) References Cited

U.S. PATENT DOCUMENTS

Figure 1:
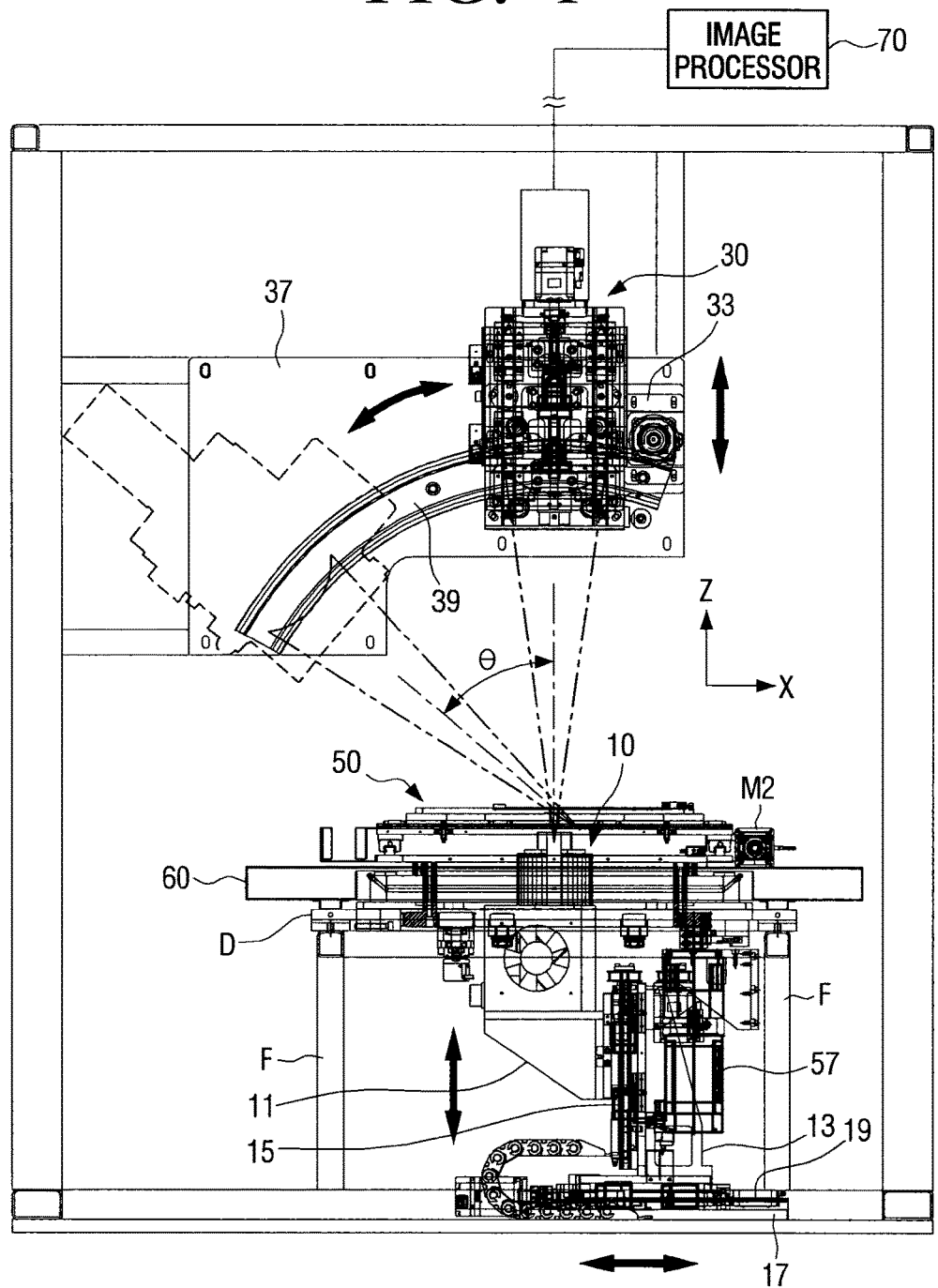

| | | | | |
|---|---|---|---|---|
| 2002/0191734 | A1* | 12/2002 | Kojima | A61B 6/037 378/4 |
| 2008/0298546 | A1* | 12/2008 | Bueno | G01V 5/0016 378/57 |
| 2009/0191735 | A1* | 7/2009 | Lin | H01R 13/72 439/131 |
| 2011/0176654 | A1* | 7/2011 | Reichel | A61B 6/56 378/4 |
| 2011/0222650 | A1* | 9/2011 | Muenker | G01N 23/046 378/20 |
| 2012/0082299 | A1* | 4/2012 | Tang | H01J 35/06 378/123 |
| 2012/0121062 | A1* | 5/2012 | Sowards-Emmerd | G06T 11/006 378/4 |

FOREIGN PATENT DOCUMENTS

| | | | |
|---|---|---|---|
| KR | 1020090031081 A | 3/2009 | |
| KR | 20090050675 A | 5/2009 | |
| KR | 100933502 B1 | 12/2009 | |
| WO | WO 2009078415 A1 * | 6/2009 | G01N 23/04 |

OTHER PUBLICATIONS

Wikipedia, "Servomechanism", (Jul. 22, 2010), Retrieved from the Internet: <http://web.archive.org/web/20100722190228/http://en.wikipedia.org/wiki/Servomotor>.*
International Search Report dated Mar. 28, 2013 corresponding to PCT/KR2012/011255, 2 pp.

* cited by examiner

AUTOMATIC X-RAY INSPECTION APPARATUS FOR SMT INLINE PROCESS

FIELD OF THE INVENTION

The present invention relates to an automatic X-ray inspection apparatus, and more particularly, to an inline automatic X-ray inspection apparatus capable of performing two-dimensional (2D) and 3D inspections on a board by automatically reading out an image scanned at high speed while maintaining high precision.

BACKGROUND ART

In general, electronic apparatuses such as wireless mobile phones or digital cameras are increasingly miniaturized, and thus mounting of a board applied to the electronic apparatuses has been miniaturized and high-densified.

As chip parts used in Surface Mount Technology (SMT) fields, 0402 types (0.4 mm×0.2 mm) are emerging, and both-sided mounting of a Ball grid array (BGA) or a chip scale package (CSP) having several hundreds of pins are becoming common. Further, as a solder bonding area (solder ball diameter) is increasingly reduced, and lead-free soldering is performed, there is no equipment for properly inspecting bonding intensity of solder bonding or the like, and thus unreliability for the inspection is increasingly growing. Further, a solder bonding portion of a rear of a package such as a BGA is not viewed with the naked eye, and since there is no pin space due to high-density, and thus the In-Circuit tester cannot be used.

Therefore, there is a need for inspection through transmissive X-ray inspection equipment with respect to the portion which is not directly checked with the naked eye as described above.

However, in response to total inspection being performed in a fabrication line, in the transmissive X-ray inspection equipment in the related art, since a professional inspector has to inspect a transmission image displayed on a screen one by one with the naked eye, variation in the determination speed and accuracy is large according to skill of the inspector and it is difficult to find bonding failure in an early stage. Therefore, it is difficult to satisfy quality guarantee desired in the markets.

To solve such problems, an automatic X-ray inspection (AXI) apparatus which can exclude the naked inspection by the inspector and automatically read out a scanned image has been suggested.

As the AXI apparatus in the related art, an oblique type which can do a computed tomography (CT) scan with respect to a mounting state of the board in a state in which an X-ray vacuum tube or a detector is obliquely disposed by representing a 2D image and a 3D image through the scanned image, so as to accurately read out internal defects (void, crack, or the like) of the board.

However, the AXI apparatus in the related art is not suitable for a SMT inline process due to low speed. This is because an image processing rate and mechanical problems are complexly acted.

In particular, in response to the mechanical problems, for example, as the X-ray vacuum tube and a stage are assembled to be integrally coupled, large load is burdened in response to moving the stage and the X-ray vacuum tube.

Further, if necessary in the inspection, since the stage is integrally assembled with the X-ray vacuum tube which has to move horizontally and vertically, due to a structure which cannot be stably supported such as occurrence of vibration in response to high-speed rotation of the stage, there are problems that rotation accuracy of the stage is considerably degraded, and concentricity of the stage is not maintained. The problems become a significant barrier to scan an object to be inspected, and thus a distorted image is formed and reliable inspection cannot be ensured.

DETAILED DESCRIPTION OF THE INVENTION

The present invention has been made in view of the above problems, and an object of the present invention is to provide an automatic X-ray inspection apparatus capable of performing 2D and 3D inspections of an object to be inspected (mounting of a board) by automatically reading out an image scanned at high speed with high accuracy so as to be applied to an SMT in line process.

Means for Solving the Problem

To obtain the above-described object, the present invention is to provide an automatic X-ray inspection apparatus includes: a stage unit configured to attachably/detachably support an object to be inspected, the stage unit being movable on an X-axis and Y-axis on a plane and rotatable; an X-ray vacuum tube arranged beneath the stage unit to irradiate the object arranged on the stage unit with X-rays; and a detector arranged above the stage unit to swivel toward one side, and configured to detect X-rays transmitted through the object. The X-ray vacuum tube swivels in synchronization with the swiveling of the detector, and an X-ray emission surface of the X-ray vacuum tube is arranged to be parallel to the stage unit. The stage unit includes a hollow shaft, and a hollow bearing configured to rotatably support the hollow shaft.

The stage unit may include a cable configured to transmit power to the stage unit, and the cable may employ a flat cable configured to prevent twisting or interference between cables. At this time, the flat cable may be windingly disposed in an outside of the hollow shaft in a spiral direction.

The flat cable may be placed on a ring-shaped cable receiving member surrounding the hollow shaft, and the cable receiving member may be formed so that a surface, on which the flat cable is placed, is a plane.

The hollow bearing may include a cross roller bearing, and an outer ring of the cross roller bearing may be clamped to a bearing housing, and an inner ring of the cross roller bearing may be clamped to the hollow shaft. Clamped points of the outer ring and inner ring may be at least three, respectively, and the three points may be set at the same angle.

The stage unit may include, to transmit the power to the stage unit, a slip ring electrically connected to the stage unit and rotating with the stage unit and a power feed brush configured to be in contact with the slip ring and apply the power.

The stage unit may receive driving force from a power transmission unit to rotate 360 degrees in a clockwise direction, and then to rotate 360 degrees in a counterclockwise direction, to do a computed tomography (CT) scan of the object. The detector may perform the scanning in response to the clockwise rotation and the counterclockwise rotation of the stage unit.

The power transmission unit may include a driving motor; a driving pulley coupled to a driving shaft of the driving motor; a driven pulley coupled along a bottom of the hollow shaft; an encoder configured to detect a rotation angel of the stage unit; and a timing belt configured to connect the driving pulley, the driven pulley, and the encoder.

The driving motor may employ a servo motor driven at a driving speed of at least 180°/sec.

The detector may perform the scanning at at least 120 frame/sec according to a signal generated by the encoder.

The X-ray vacuum tube may maintain a separated state from the stage unit, and move vertically and horizontally.

The detector may convert X-rays, which transmit the object and are ionized, into an electrical signal, amplify the converted electrical signal, and convert the amplified signal into a digital image signal. The present invention may further include an image processor configured to perform high-seed reconstruction on a plurality of digital image signals transferred from the detector, and then perform 3D inspection. At this time, the image processor may include at least four graphics processing unit (GPU) cores to perform the high-speed reconstruction.

Effect of the Invention

As described above, since the present invention scans twice image as compared to the related art while maintaining rotation accuracy in response to high-speed rotation of the stage unit, and may enable bidirectional scanning in the clockwise and counter clockwise rotations of the stage unit, the present invention may significantly improve inspection speed and be applied to a SMT inline process with high-speed processing using a plurality of GPU cores.

Further, the present invention may use a hollow bearing and set at least three clapping points disposed at the same angle so as to minimize deformation of the hollow bearing, and thus maintain concentricity with respect to a rotation shaft of the stage unit.

The present invention may use a flat cable or include a slip ring and a power feed brush to minimize interference with respect to the rotation of the stage unit.

BRIEF DESCRIPTIONS OF THE DRAWINGS

Figure 2:
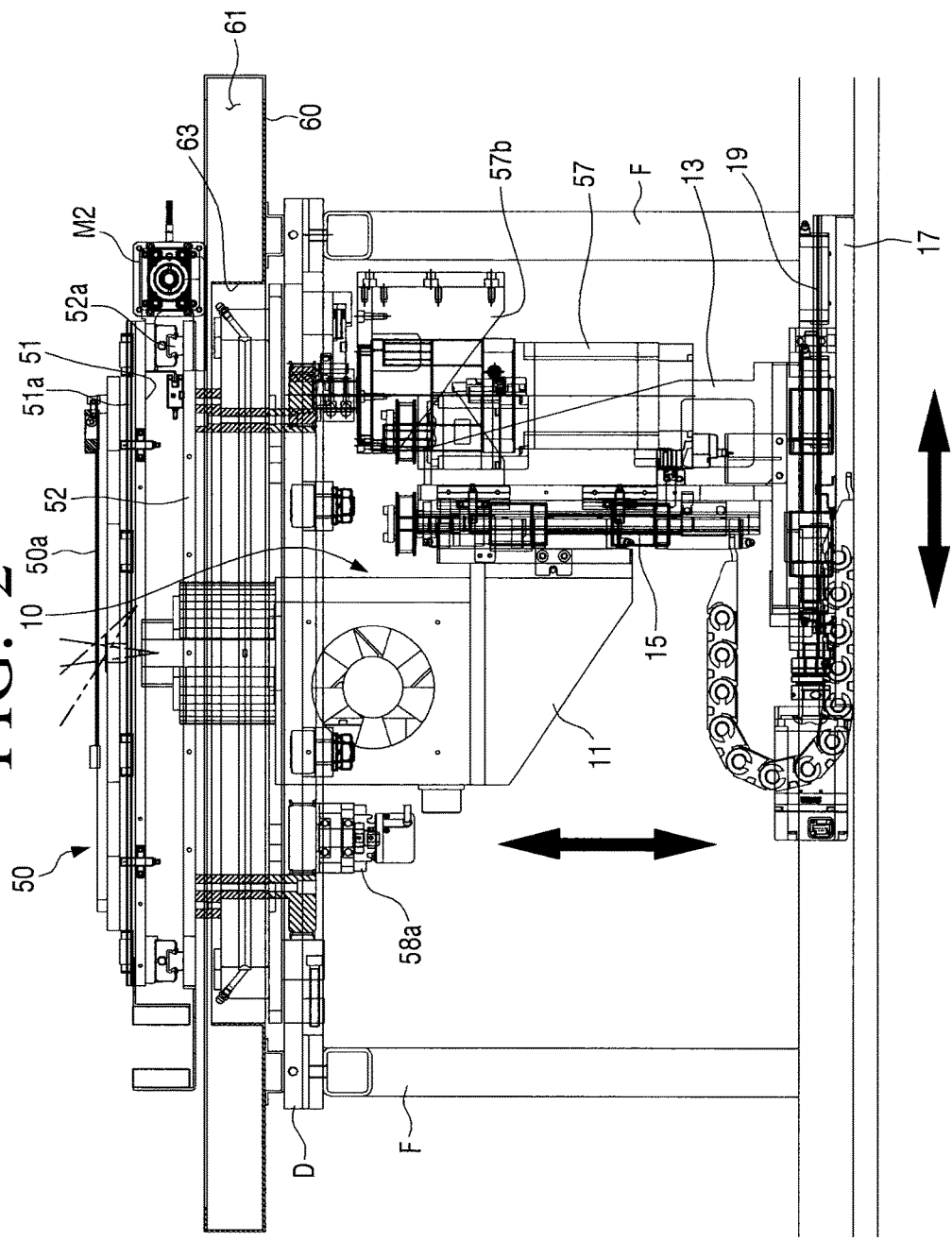
Figure 3:
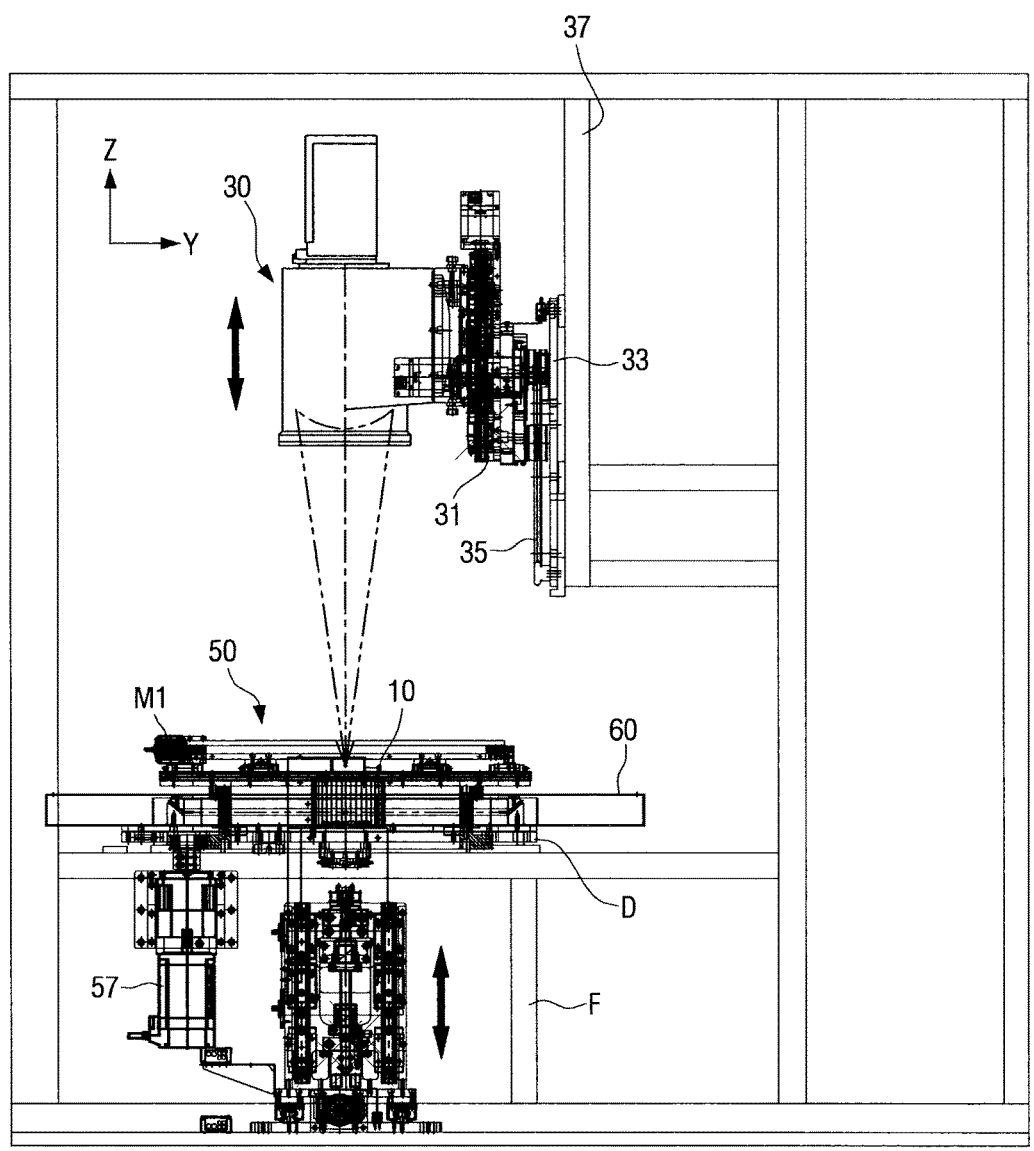
Figure 4:
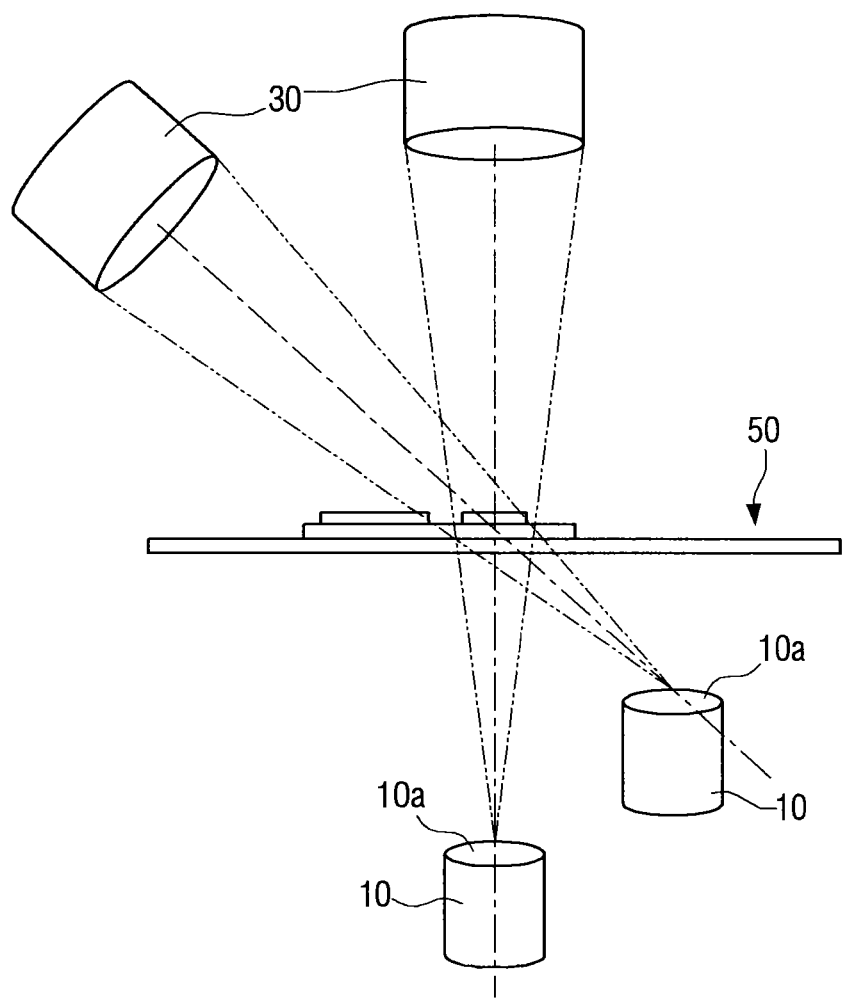
Figure 5:
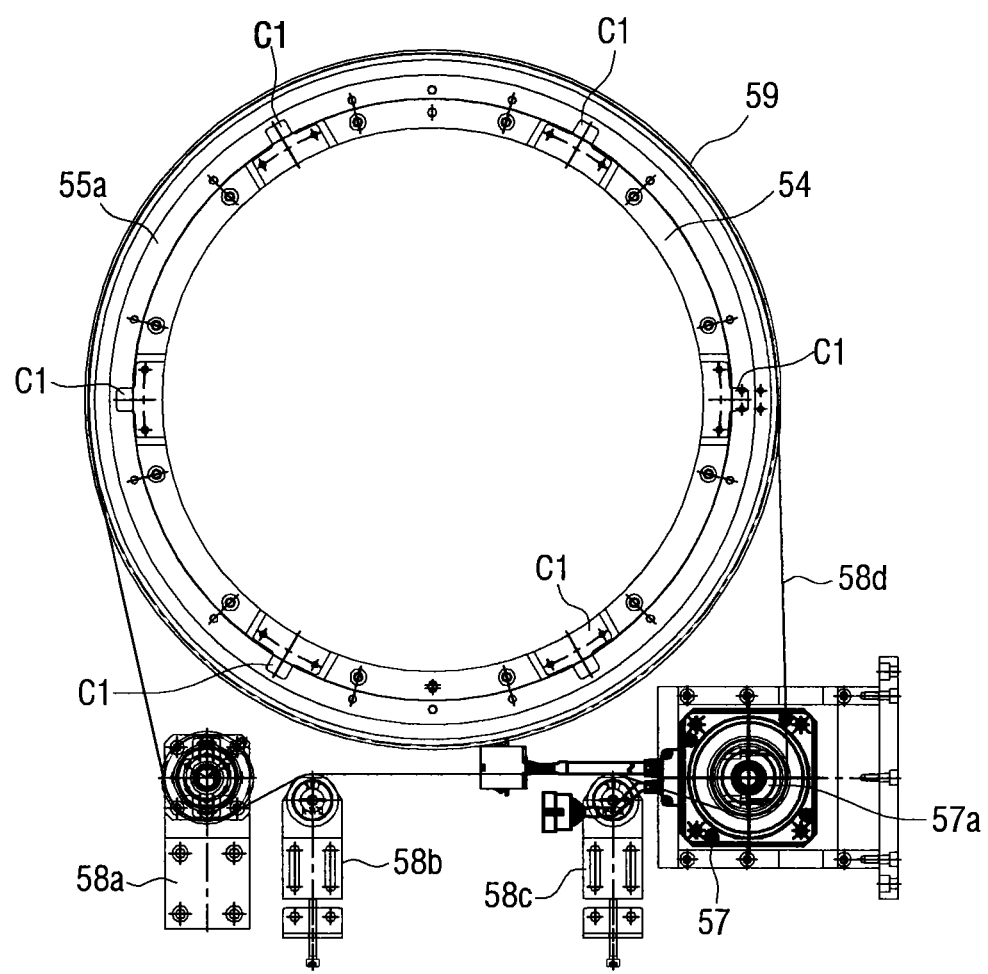
Figure 6:
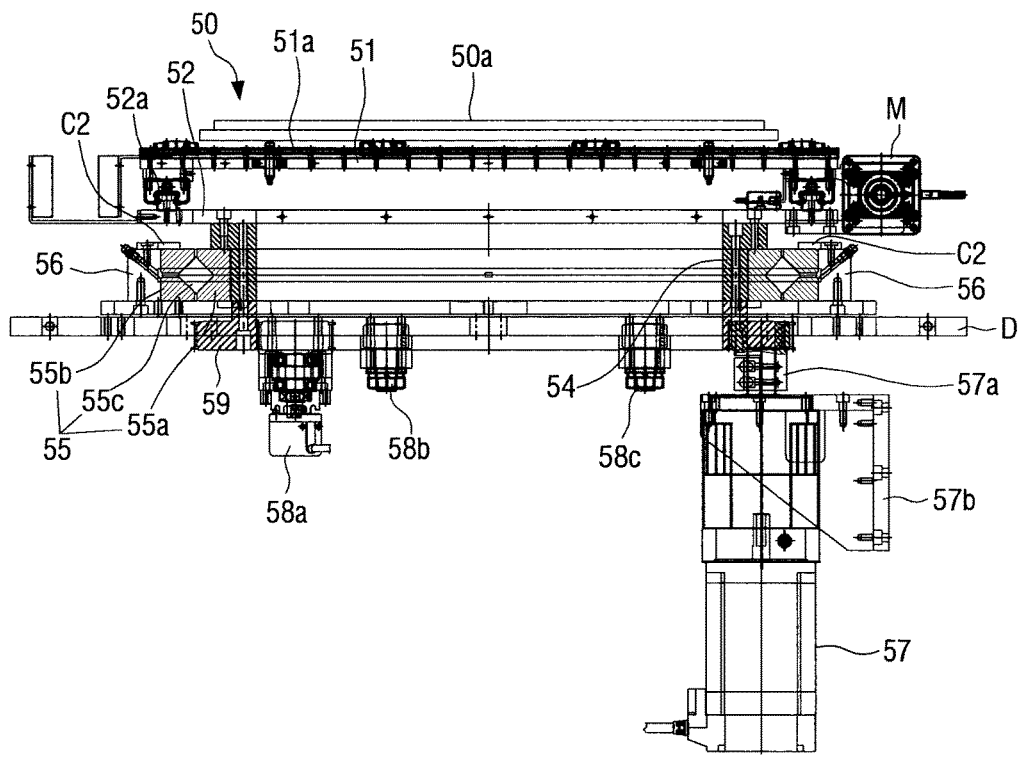
Figure 7:
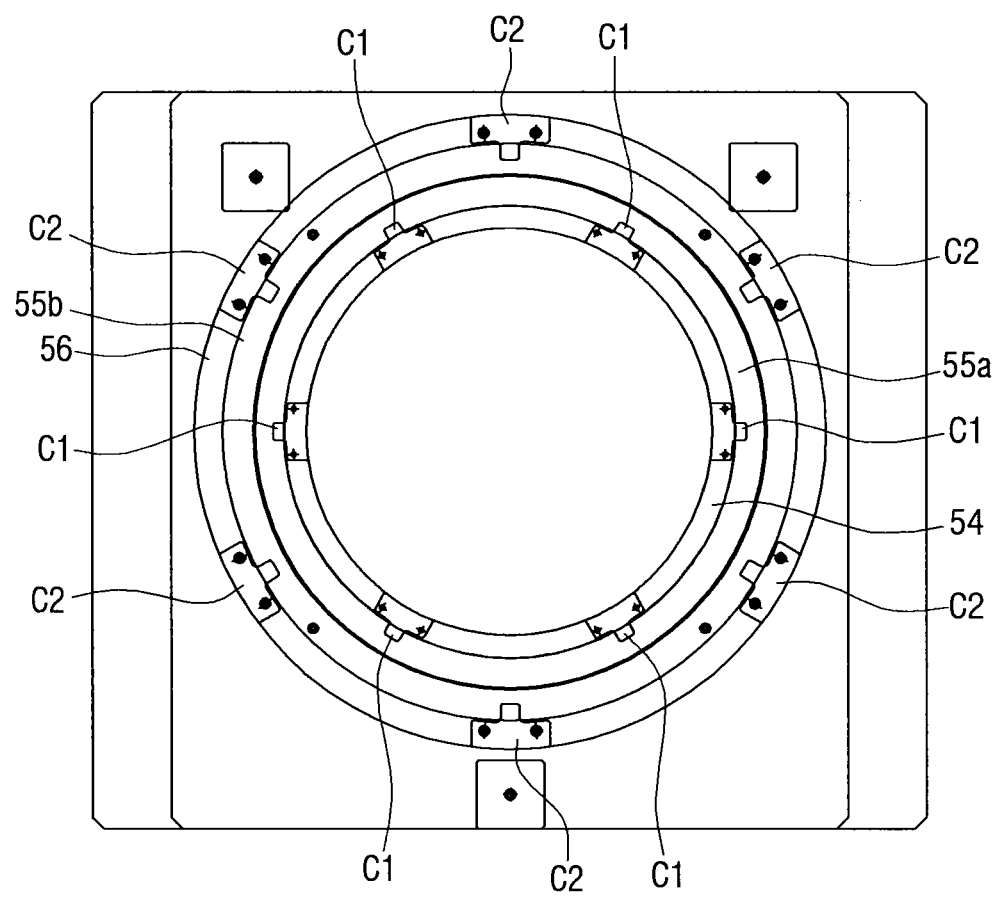
Figure 8:
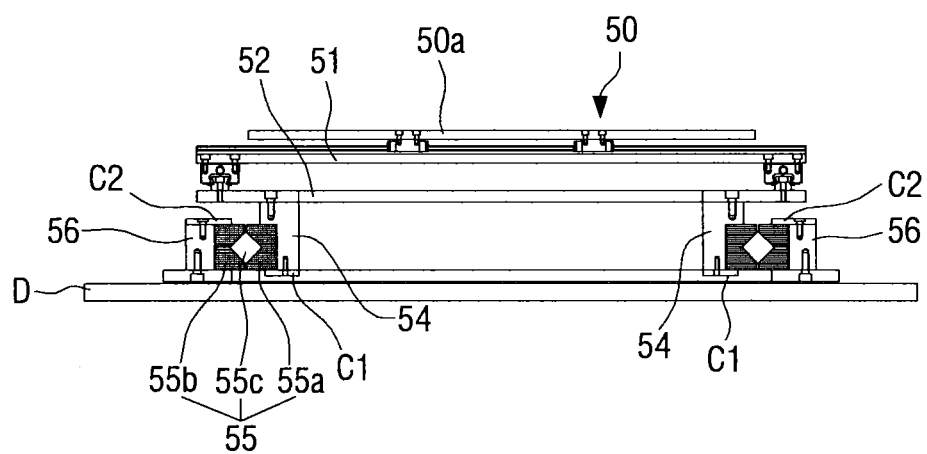
Figure 9:
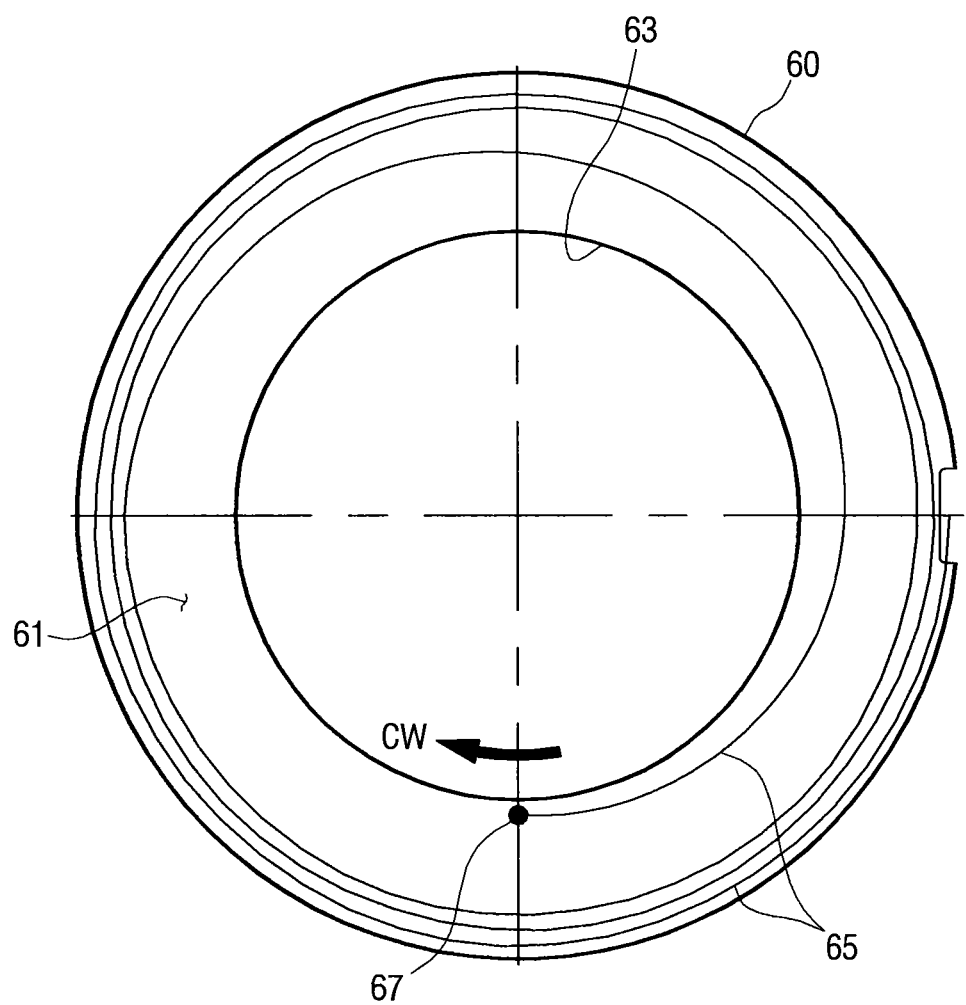
Figure 10:
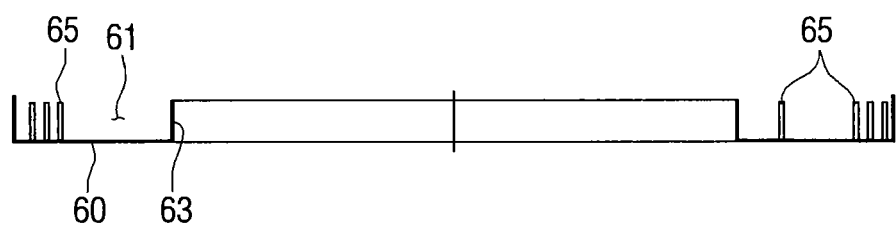
Figure 11:
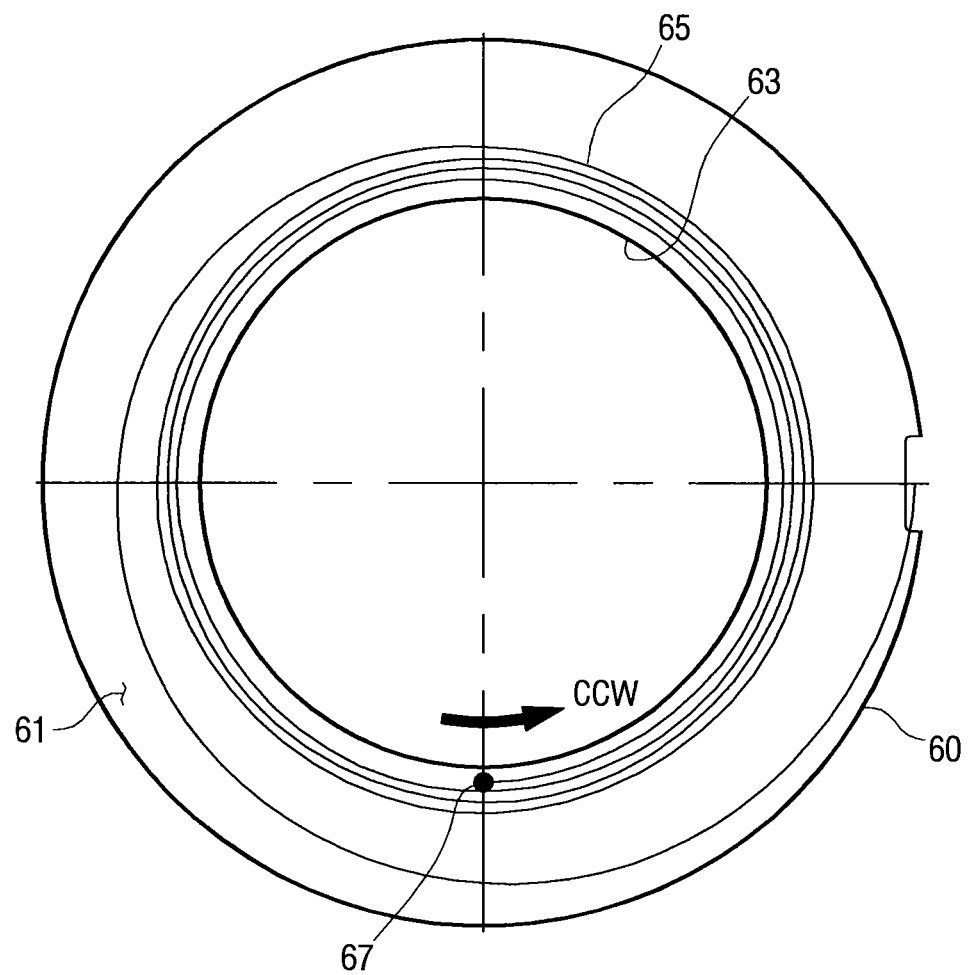
Figure 12:
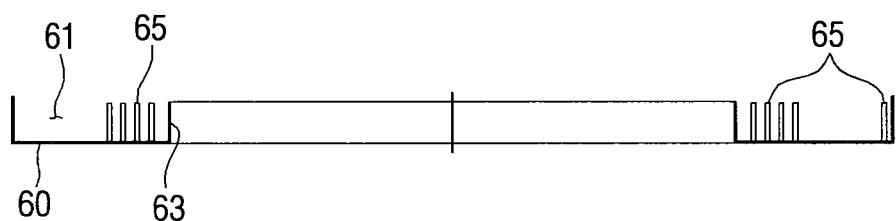
Figure 13:
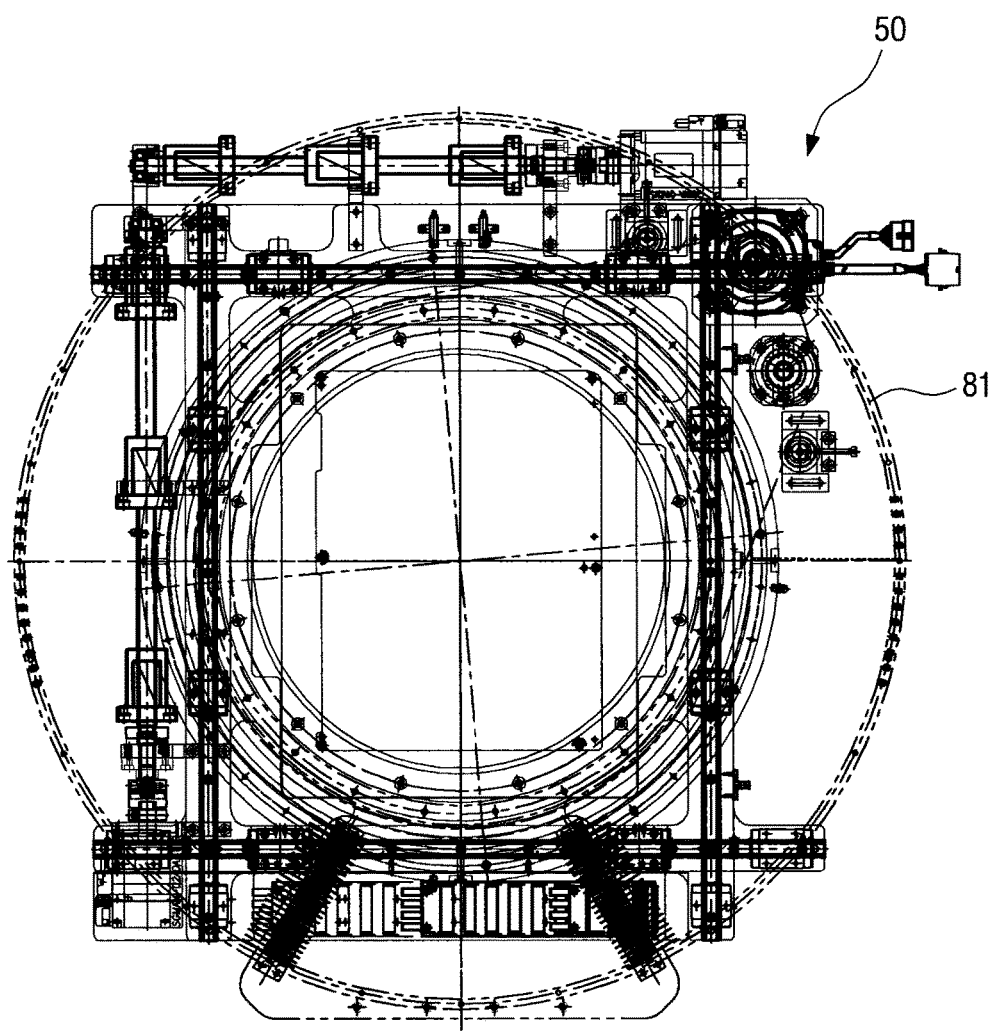
Figure 14:
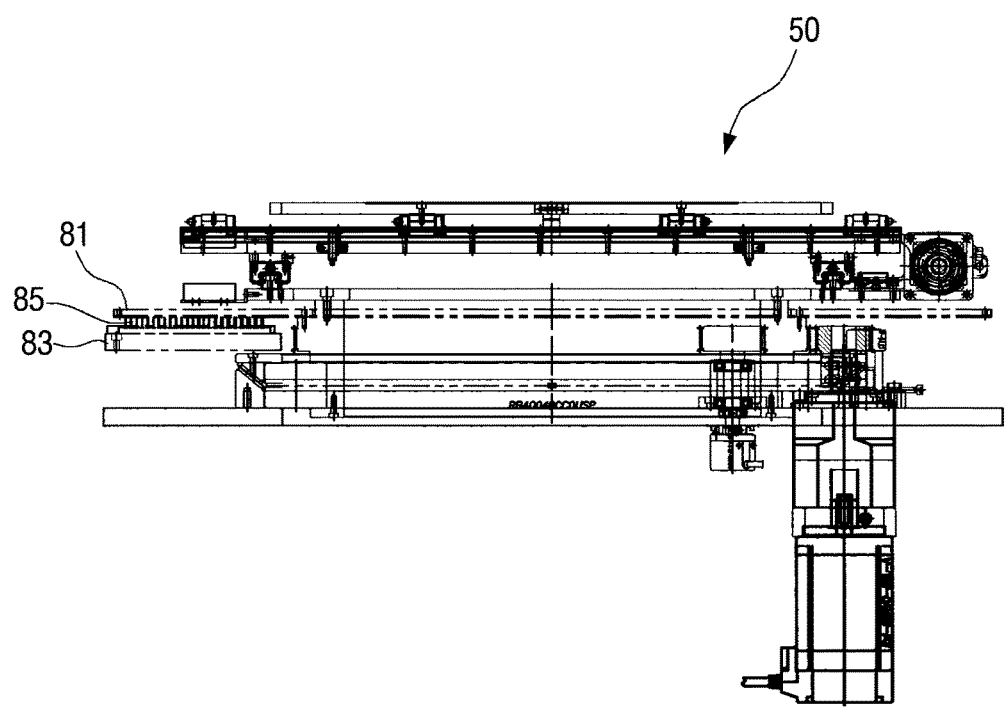

FIG. 1 is a front view illustrating an automatic X-ray inspection apparatus for an SMT inline process according to an embodiment of the present invention, FIG. 2 is an enlarged view illustrating a stage unit and an X-ray vacuum tube illustrated in FIG. 1, FIG. 3 is a side view illustrating an automatic X-ray inspection apparatus for an SMT inline process according to an embodiment of the present invention, FIG. 4 is a schematic diagram illustrating synchronization movements of an X-ray vacuum tube and a detector illustrated in FIG. 1, FIGS. 5 and 6 are a plan view and a side view illustrating a power transmission unit of a stage unit, FIGS. 7 and 8 are a plan view and a side view illustrating a baring structure of a stage unit, FIGS. 9 and 10 are a plan view and a side view illustrating an arrangement of a flat cable before a stage unit rotates, FIGS. 11 and 12 are a plan view and a side view illustrating an arrangement of a flat cable after a stage unit rotates 360 degrees, and FIGS. 13 and 14 are a plan view and a side view illustrating an example in which power is supplied to a stage unit using a slip ring and a power feed brush.

MODE FOR CARRYING OUT THE INVENTION

Hereinafter, an automatic X-ray inspection apparatus for an SMT inline process according to an embodiment of the present invention will be described with reference to the accompanying drawings. Merely, well-known technology related to the present invention is not described in detail since they would obscure the present invention with unnecessary detail Referring to FIGS. 1 to 3, an automatic X-ray inspection apparatus for an SMT inline process of the embodiment is an inspection apparatus which may perform both 2D inspection and 3D inspection, and includes an X-ray vacuum tube 10, a detector 30, a stage unit 50, and an image processor 70.

The X-ray vacuum tube 10 accelerates electrons heat-emitted from a filament in the tube to a high voltage between metals such as tungsten, molybdenum, or copper, allows the accelerated electrons to collide with a metal target, and generates X-rays.

The X-ray vacuum tube 10 is vertically arranged beneath the stage unit 50, and an X-ray emission surface 10a of a top of the X-ray vacuum tube 10 is always arranged to be parallel to the stage unit 50 (see FIGS. 4).

Such an X-ray vacuum tube 10 is installed to be movable horizontally and vertically, and the movement is performed according to driving of a first supporter 11 and a second supporter 13.

The first supporter 11 is fixed to and installed in one side of the X-ray vacuum tube 10, and sildably coupled to a vertical guide rail 15 of the second supporter 13. The second supporter 13 is slidably coupled to a horizontal guide rail 19 of a third supporter 17. At this time, the horizontal guide rail 19 may be arranged along a straight direction corresponding to a swiveling direction of the detector 30, that is, an X-axis direction, so that the X-ray vacuum tube 10 may move in synchronization with swiveling of the detector 30.

As described above, as the X-ray vacuum tube 10 is driven in a completely separated state from the stage unit 50, since large load is not burdened in response to moving of the X-ray vacuum tube 10 as compared to the related art, the present invention may smoothly move the X-ray vacuum tube 10 through little driving force.

The detector 30 converts X-rays, which transmit each mounting part of a board which is an object to be inspected and are ionized, into an electrical signal, amplifies the converted electrical signal, and converts the amplified signal into a digital image signal.

The detector 30 is arranged over the stage unit 50 to be spaced at certain intervals, and installed to be swiveled at a certain degree θ to one direction. At this time, a fourth supporter 31 is fixed and coupled to one side of the detector 30, and is sildably coupled to a guide rail 35 of a fifth supporter 33. The fifth supporter 33 is slidably movably coupled along a curved guide groove 39 formed in an upper guide plate 37.

Referring to FIG. 4, the detector 30 is vertically arranged so that the center of the detector 30 coincides with the center of the X-ray emission surface 10a of the X-ray vacuum tube in an initial state. Further, the detector 30 swivels at a certain angel and moves in the CT scan, and the X-ray vacuum tube 10 also moves in synchronization with the swiveling of the detector 30. At this time, a central location of the swiveling of the detector 30 is set to a location corresponding to a height of the stage unit, and the emission surface 10a of the X-ray vacuum tube 10 which moves in synchronization with the swiveling of the detector 30 is kept to be parallel to the stage unit 50.

The stage unit 50 includes an object support member 50a, a hollow shaft 54, a hollow bearing 55, a driving motor 57, a power transmission unit, and a cable receiving member 60.

The object support member 50a detachably/attachably supports the board, which is the object to be inspected, through a conventional clamping unit. The object support member 50a has a space formed in an inner side thereof to transmit X-rays. The object support member 50a straightly moves on a plane to an X-axis and Y-axis directions.

The stage unit 50 includes first and second support frames 51 and 52 to move the object support member 50a to the X-axis and Y-axis directions. At this time, the object support member 50a is slidably coupled to an X-axis guide rail 51a on the first support frame 51, and the first support frame 51 is slidably coupled to a Y-axis guide rail 52a on the second support frame 52. The object support member 50a and the first support frame 51 receive driving forces from driving motors M1 and M2, respectively.

The hollow shaft 54 is coupled to a bottom of the second support frame 52, and rotatably supported by the hollow bearing 55 surrounding an outer circumference of the hollow shaft 54.

Referring to FIGS. 7 and 8, the hollow bearing 55 is supported by the bearing housing 56 surrounding an outer circumference of the hollow bearing 55. Such a hollow bearing 55 may use a cross roller bearing including an inner ring 55a, an outer ring 55b, and a roller 55c arranged between the inner ring 55a and the outer ring 55b.

At this time, the inner and outer rings 55a and 55b are fixed by a plurality of first and second clamps C1 and C2 fixed to and installed in the hollow shaft 54 and the bearing housing 56, respectively. Thus, the inner ring 55a is fixed to the hollow shaft 54 and rotates with the hollow shaft 54, and the outer ring 55b is fixed to the bearing housing 56 and does not rotate.

The plurality of first clamps C1, which clamps the inner ring 55a, are arranged at the same interval, and similarly, the plurality of second clamps C2, which clamps the outer ring 55b, are arranged at the same interval. In the embodiment, although six first clamps C1 and six second clamps C2 are used, the present invention is not limited thereto, and at least three first clamps C1 and at least three second clamps C2 may be used. Merely, the plurality of used first and second clamps C1 and C2 may be arranged at the same angle, respectively.

As described above, as the inner ring 55a and the outer ring 55b of the hollow bearing 55 are point-supported at certain locations, deformation applied to the hollow bearing 55 may be minimized, and thus rotation accuracy of the stage unit 50 may be ensured.

The bearing housing 56 is fixed to and installed in a top surface of a die D horizontally arranged. At this time, the die D is supported by a plurality of vertical frames F, and located at a certain height from a bottom surface. Preferably, the height of the die D is set to an appropriate height by considering a movement range of the X-ray vacuum tube 10.

Referring to FIGS. 5 and 6, the driving motor 57 alternately rotates 360 degrees the stage unit 50 through a power transmission unit to a clockwise direction and a counterclockwise direction, and may use a high-speed server motor having a driving speed of at least 180°/sec or more.

The driving motor 57 is fixed to and installed in any one of the plurality of vertical frames F by a support member 57b, and a driving pulley 57a connected to a timing belt 58d is coupled to a rotation shaft (not shown) of the driving motor 57.

At this time, the timing belt 58d is connected to a driven pulley 59 connected along a bottom of the hollow shaft 54 and an encoder 58a configured to detect a rotation angle of the stage unit 50. At this time, the timing belt 58d may maintain an appropriate belt tension as at least portion of the timing belt 58d is pressed by a pair of belt tension adjusting units 58b and 58c.

The encoder 58a generates a signal whenever the stage unit 50 rotates 1.5 degrees, and the detector 30 scans the rotating object at 120 frame/sec according to the signal. Therefore, a large number of projections may be acquired through the high-speed scanning as compared to the related art, and thus more accuracy and abundant image quality may be obtained. Therefore, the detector 30 may scan 240 frames with respect to one portion of substrate mounting in response to rotating 360 degrees to a clockwise direction, and after the detector moves to the other portion of the substrate mounting to be scanned to an X-axis direction and a Y-axis direction, the detector may scan 240 frames in response to the object rotating 360 degrees to an original location to a counterclockwise direction.

The embodiment has been exemplified that the scanning speed of the detector 30 is 120 frame/sec, but the present invention is not limited thereto, and any detector implemented to have the scanning speed of at least 120 frame/sec or more may be used.

In this regard, in the related art, the scanning is performed on the object in response to rotating from 0 degree to 360 degrees to a clockwise direction, and the scanning is not performed in response to rotating to an original location again, that is, during the rotating 360 degrees to a counterclockwise direction. Therefore, loss occurs by the rotation time.

Thus, the related art has a structure which can perform only unidirectional scanning, but the present invention may perform bidirectional scanning (clockwise direction and counterclockwise direction), and improvement in productivity may be expected.

Further, the cable receiving member 60 is fixed to and installed in the die D, and the cable receiving member 60 is arranged to surround the bearing housing 56. A ring-shaped receiving space 61, in which a flat cable 65 is flowably placed, is formed in the cable receiving member 60, and a through hole 63, into which the bearing housing 56 is inserted, is formed in the center of the cable receiving member 60. At this time, a bottom surface of the receiving space 61 is formed in a plane, and one end 67 of the flat cable 65 close to the hollow shaft 54 is fixed to the cable receiving member 60.

Referring to FIGS. 9 to 12, the flat cable 65 is windingly arranged along the receiving space 61 of the cable receiving member 60 to a spiral direction so as to prevent twisting or interference between cables.

The windingly arrangement of the flat cable 65 in the spiral direction may minimize a contact area with a bottom surface of the receiving space 61 and reduce friction force in response to the flat cable 65 moving in the receiving space 61 according to the rotation of the stage unit 50 to the clockwise direction (see FIGS. 11 and 12) and to the counterclockwise direction (see FIGS. 9 and 10). Thus, a rotation interference factor of the state unit 50, which may occur by the flat cable 65, is minimized so that the rotation accuracy may be maintained in response to the stage unit 50 rotating at high speed.

As described above, the example in which the stage unit 50 receives power through the flat cable 65 has been described, but the present invention is not limited thereto, and the flat cable 65 will be omitted. That is, referring to FIGS. 13 and 14, the stage unit 50 includes a slip ring 81 rotating with the stage unit 50, and a power feed brush 83 which bring a plurality of contact pins 85 in contact with a circular conductive pattern (not shown) formed in one surface of the slip ring 81 and applies electricity to the slip ring 81, so that flat cable 65 may be omitted.

At this time, since the flat cable 65 may be omitted, the factor, which may degrade rotation accuracy, may be minimized in response to high-speed rotation of the stage unit 50.

The image processor 70 may include at least four graphics processing unit (GPU) cores, and perform high-speed reconstruction on the projections scanned by the detector 50 through the GPU cores so that the present invention may reduce 3D inspection time to approximately three seconds per one point of the object, and thus the present invention may be used for a SMT inline process.

Further, in the present invention, the concentricity of the rotation shaft of the stage unit 50 affects to obtain high-quality image. In particular, a variation in the concentricity may occur due to mechanical problems, and the image processor 70 automatically correct the variation which mechanically occurs. The automatic correction is performed in software, and the automatic correction is performed by registering a pattern having uniqueness in the rotation center of the stage unit 50, finding a tolerance offset which occurs every 1.5 degrees in the 360-degree rotation, and simultaneously performing reconstruction and correction.

On the other hand, the general X-ray inspection apparatus requires a certain time for stabilizing a current/voltage and a temperature of a target in response to turning on the X-ray voltage/current for equipment operation after the X-ray voltage/current is turned off, and this is represented by the phenomenon in which a focus of an image acquired through X-rays is changed according to a rising step of the temperature of the target. The present invention may apply an auto tube focus (ATF) which finds a focus of an image in real time to omit the time required for the stabilization and simultaneously to improve productivity.

Further, the oblique CT of the related art employs an open type X-ray vacuum tube which may improve geometric magnification in order to resolve an X-ray irradiation angle problem. The present invention may use a close type X-ray vacuum tube to reduce a volume of the vacuum tube, so that costs may be reduced, and at the same time, a configuration of a mechanism may be simply implemented. At this time, the present invention may apply a wide angle close tube having an irradiation angle of one-side 60 degrees to solve the above-described X-ray irradiation problem.

The foregoing exemplary embodiments and advantages are merely exemplary and are not to be construed as limiting the present inventive concept. The description of the exemplary embodiments is intended to be illustrative, and not to limit the scope of the claims, and many alternatives, modifications, and variations will be apparent to those skilled in the art.

INDUSTRIAL APPLICABILITY

The present invention relates to an inline automatic X-ray inspection apparatus and may apply non-destructive inspection fields of electronic parts such as semiconductor chips.

The invention claimed is:

1. An automatic X-ray inspection apparatus, comprising:
   a stage unit configured to attachably/detachably support an object to be inspected, the stage unit being movable on an X-axis and Y-axis on a plane and rotatable and includes a flat cable configured to transmit power to the stage unit;
   an X-ray vacuum tube arranged beneath the stage unit to irradiate the object arranged on the stage unit with X-rays;
   a detector arranged above the stage unit to swivel toward one side, and configured to detect X-rays transmitted through the object; and
   an image processor configured to perform high-speed reconstruction on a plurality of digital image signals transferred from the detector, and then perform three-dimensional (3D) inspection, the image processor including at least four graphics processing unit (GPU) cores to perform the high-speed reconstruction,
   wherein the X-ray vacuum tube swivels in synchronization with the swiveling of the detector, and an X-ray emission surface of the X-ray vacuum tube is arranged to be parallel to the stage unit,
   the stage unit includes a hollow shaft, and a hollow bearing configured to rotatably support the hollow shaft,
   the detector converts the X-rays, which transmit the object and are ionized, into an electrical signal, amplifies the converted electrical signal, and converts the amplified electrical signal into a digital image signal, and
   wherein the flat cable is windingly disposed in an outside of the hollow shaft in a spiral direction and is placed on a ring-shaped cable receiving member surrounding the hollow shaft, and the cable receiving member is formed so that a surface, on which the flat cable is placed, is a plane.

2. The automatic X-ray inspection apparatus according to claim 1, wherein the hollow bearing includes a cross roller bearing, and an outer ring of the cross roller bearing is clamped to a bearing housing, and an inner ring of the cross roller bearing is clamped to the hollow shaft.

3. The automatic X-ray inspection apparatus according to claim 2, wherein clamped points of the outer ring and inner ring are at least three, respectively, and the three points are set at the same angle.

4. The automatic X-ray inspection apparatus according to claim 1, wherein the stage unit includes: to transmit the power to the stage unit, a slip ring electrically connected to the stage unit and rotating with the stage unit; and a power feed brush configured to be in contact with the slip ring and apply the power.

5. The automatic X-ray inspection apparatus according to claim 1, wherein the stage unit receives driving force from a power transmission unit to rotate 360 degrees in a clockwise direction, and then to rotate 360 degrees in a counter-clockwise direction, to do a computed tomography (CT) scan of the object, and the detector performs the scanning in response to the clockwise rotation and the counterclockwise rotation of the stage unit.

6. The automatic X-ray inspection apparatus according to claim 5, wherein the power transmission unit includes:
   a driving motor;
   a driving pulley coupled to a driving shaft of the driving motor;
   a driven pulley coupled along a bottom of the hollow shaft;
   an encoder configured to detect a rotation angel of the stage unit; and
   a timing belt configured to connect the driving pulley, the driven pulley, and the encoder.

7. The automatic X-ray inspection apparatus according to claim 6, wherein the driving motor is a servo motor driven at a driving speed of at least 180°/sec.

8. The automatic X-ray inspection apparatus according to claim 7, wherein the detector performs the scanning at at least 120 frame/sec according to a signal generated by the encoder.

9. The automatic X-ray inspection apparatus according to claim 1, wherein the X-ray vacuum tube maintains a separated state from the stage unit, and moves vertically and horizontally.

* * * * *